United States Patent [19]
Oude Alink

[11] 3,935,215
[45] Jan. 27, 1976

[54] PROCESS OF REVERTING THIOPHOSPHATES

[75] Inventor: Bernardus A. Oude Alink, St. Louis, Mo.

[73] Assignee: Petrolite Corporation, St. Louis, Mo.

[22] Filed: June 29, 1973

[21] Appl. No.: 374,992

Related U.S. Application Data

[62] Division of Ser. No. 165,336, July 22, 1971.

[52] U.S. Cl...... 260/327 C; 260/240 R; 260/240 D; 260/294.8 D; 260/947; 252/8.55 E; 134/3
[51] Int. Cl.² .................................... C07D 339/04
[58] Field of Search .............................. 260/327 C

[56] References Cited
OTHER PUBLICATIONS
Breslow, et al., The Chemistry of Heterocyclic Compounds, pp. 352–366, (Interscience, 1966).

Primary Examiner—Henry R. Jiles
Assistant Examiner—C. M. S. Jaisle
Attorney, Agent, or Firm—Sidney B. Ring; Hyman F. Glass

[57] ABSTRACT

Thiophosphates of the formula

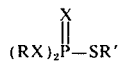

where X is 0 or S, R is a hydrocarbon or a substituted hydrocarbon group such as alkyl, aryl, cycloalkyl, alkaryl, aralkyl, etc., and R' is a 3-thione-propene-1 or a substituted 3-thione-propene-1 group; the preparation thereof by reacting a 1,2-dithiolium compound with a phosphite ester; the reversion to the original dithionium compound is effected by reacting the thiophosphate under acid conditions; and the uses of such thiophosphates as corrosion inhibitors in acid systems.

7 Claims, No Drawings

PROCESS OF REVERTING THIOPHOSPHATES

This application is a division of Ser. No. 165,336 filed July 22, 1971.

This invention relates to S-(3-thione-propene-1) thiophosphates, the preparation thereof, and uses therefor.

1,2-dithiole-3-thiones are known compounds prepared by a variety of methods. Examples of such compounds, and methods for their preparation, are disclosed in THE CHEMISTRY OF HETEROCYCLIC COMPOUNDS, "Multi-Sulfur and Sulfur and Oxygen Five-and Six-Membered Heterocycles," PART 1, pages 352–366, by David S. Breslow et al., Interscience Publishers, 1966.

1,2-dithiole-3-thiones may be expressed by the formula:

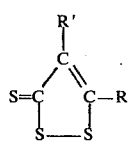

where R and R' are substituted groups, for example, alkyl, aryl, cycloalkyl, alkenyl, alkynyl, alkaryl, aralkyl, heterocyclic, etc. In addition, one of the above R's may be hydrogen. Examples of a wide variety of 1,2-dithiole-3-thiones are presented in the above text by Breslow et al. in Table 4, pages 352–366, which is incorporated into this application as if part hereof.

1,2-dithiole-3-thiones are conveniently prepared by the classic method of reacting an olefin with sulfur, for example, according to the following equation:

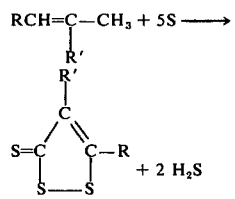

The olefin employed in the reaction contains
1. a reactive double bond
2. a primary carbon atom
3. at least four hydrogen atoms on the 3 terminal carbons with at least one hydrogen on the carbon beta to primary carbon atom This reaction is carried out at any suitable temperature and time, for example, at about 100° to 300°C., such as from about 140° to 240°C. but preferably from about 160° to 220°C. for a period of about 2 to 160 hours, and about 10 to 50 hours, but preferably about 15 to 40 hours.

The following examples are presented by way of illustration and not of limitation to show the preparation of 1,2-dithiole-3-thiones which may be employed as starting materials to prepare the dithiolium compounds of this invention.

EXAMPLE 1A

The Preparation of 4-phenyl-1,2-dithiole-3-thione

In a suitable reactor equipped with a stirrer, thermometer and a reflux condenser, was placed 118 g of methyl-styrene and 48 g of sulfur. The mixture was heated for 37 hours at 200°–210°C. After the reaction was completed, the mixture was slowly cooled to room temperature. The product was collected and crystallized from benzene, red crystals, (32 grams, 50 percent yield), m.p. 122°–124°C.

EXAMPLE 2A

Preparation of 4-(3-methoxy-4-hydroxy)phenyl-1,2-dithiole-3-thione

In a suitable reactor equipped with a stirrer, thermometer, addition funnel and reflux condenser was placed 32 g of sulfur, 1.0 g of di-o-tolylguanidine as catalyst and 150 cc of mesitylene as solvent. The mixture was brought to a reflux (170°C.) and over a 1 hour period 66 g of isoeugenol

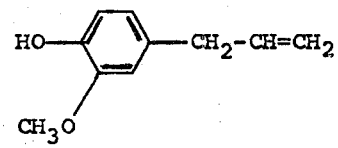

was added dropwise. Reflux was continued for 48 more hours. The mesitylene was decanted from the solid. The solid was treated twice with 500 cc portion of a 5% aqueous potassium hydroxide solution. Upon acidification the product precipitated as a brown solid.

EXAMPLE 3A

Preparation of 4-neopentyl-5-t-butyl-1,2-dithiole-3-thione

To a mixture of 320 g of sulfur and 6.0 g of di-o-tolylguanidine was added over a 9 hour period, at a reaction temperature of 210°–215°C., 226 g of triisobutylene,

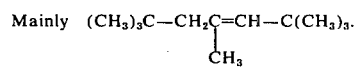

Mainly $(CH_3)_3C-CH_2\underset{CH_3}{\overset{|}{C}}=CH-C(CH_3)_3$.

Heating at 210°–215°C. was continued for an additional 14 hours. The product was distilled and there was collected 220 g of 4-neopentyl-5-t-butyl-1,2-dithiole-3-thione, b.p. 155°–185°C. (3–4 mm Hg).

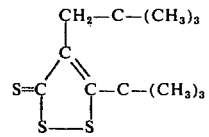

EXAMPLE 4A

Preparation of 4,5-tetramethylene-1,2-dithiole-3-thione

In a suitable reactor equipped with a stirrer, reflux condenser, thermometer and addition funnel was placed 24 g of sulfur, 171 g of carbon disulfide and 150 cc of dimethyl formamide. The mixture was cooled to 0°C. and under continuous stirring and cooling 132 g of 1-morpholino-1-cyclohexene was introduced over a ½ hour period. After the addition was completed, stirring was continued for an additional 16 hours. The resulting slurry was poured into water and the resulting orange solid crystallized from acetone, m.p. 95°–97°C. Yield 37 percent.

The following table presents illustrative 1,2-dithiole-3-thiones of the formula

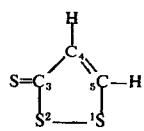

The radical indicated replaces the H's in the 4th and/or 5th positions as indicated.

TABLE I

| | |
|---|---|
| 1) | 4-$CH_3$ |
| 2) | 5-$CH_3$— |
| 3) | 4-$C_2H_5$— |
| 4) | 5-$C_2H_5$— |
| 5) | 4-$(CH_3)_3CCH_2$— |
| 6) | 5-$n$-$C_{17}H_{35}$— |
| 7) | 4-$C_6H_5$— |
| 8) | 5-$C_6H_5$— |
| 9) | 4-($p$-$CH_3C_6H_4$—) |
| 10) | 5-($p$-$CH_3C_6H_4$—) |
| 11) | 4-($p$-$C_2H_5C_6H_4$—) |
| 12) | 4-($p$-$t$-$C_4H_9C_6H_4$—) |
| 13) | 4-($p$-$t$-$C_5H_{11}C_6H_4$—) |
| 14) | 5-($p$-$C_6H_5$—$C_6H_4$—) |
| 15) | 5-($p$-$ClC_6H_4$—) |
| 16) | 5-($p$-$BrC_6H_4$—) |
| 17) | 5-($p$-$IC_6H_4$—) |
| 18) | 4-($p$-$CH_3OC_6H_4$—) |
| 19) | 5-($o$-$CH_3OC_6H_4$—) |
| 20) | 5-($p$-$CH_3OC_6H_4$—) |
| 21) | 5-($p$-$HOC_6H_4$—) |
| 22) | 5-($p$-$CH_3CO_2C_6H_4$—) |
| 23) | 5-[$p$-$(CH_3)_2NC_6H_4$—] |
| 24) | 5-[2,4-$(CH_3)_2C_6H_3$—] |
| 25) | 5-(2-$CH_3O$-5-$CH_3C_6H_3$—) |
| 26) | 5-[2,3-$(CH_3O)_2C_6H_3$—] |
| 27) | 5-[2,5-$(CH_3O)_2C_6H_3$—] |
| 28) | 5-[3,4-$(CH_3O)_2C_6H_3$—] |
| 29) | 5-(3-$CH_3O$-4-$HOC_6H_3$) |
| 30) | 5-(2-HO-3-$CH_3OC_6H_3$—) |
| 31) | 5-(3-$CH_3O$-4-$CH_3O_2CCH_2OC_6H_3$—) |
| 32) | 5-[3,4-$(HO)_2C_6H_3$—] |
| 33) | 5-[3,4-$(CH_3CO_2)_2C_6H_3$—] |
| 34) | 5-(3,4-Methylenedioxyphenyl-) |
| 35) | 5-(3,4,5-$I_3C_6H_2$—) |
| 36) | 4-(1-Naphthyl-) |
| 37) | 4-(1-Naphthyl-) |

38) 4

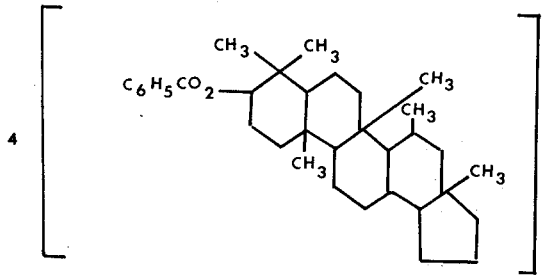

39) 4

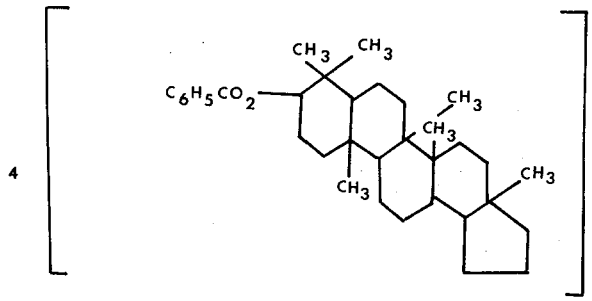

TABLE I-continued

| | |
|---|---|
| 40) | 5-(2-Furyl-) |
| 41) | 4-(2-Thienyl-) |
| 42) | 5-(2-Thienyl-) |
| 43) | 4-(4-CH$_3$-2-thienyl-) |
| 44) | 5-(5-CH$_3$-2-thienyl-) |
| 45) | 5-(5-C$_2$H$_5$-2-thienyl-) |
| 46) | 4-[3,4-(CH$_3$)$_2$-2-thienyl-] |
| 47) | 5-(2-Pyridyl-) |
| 48) | 5-(3-Pyridyl-) |
| 49) | 5-(4-Pyridyl-) |
| 50) | 5-(C$_6$H$_5$CH=CH—) |
| 51) | 5-(p-CH$_3$OC$_6$H$_4$CH=CH—) |
| 52) | 5-(2-Furyl-CH=CH—) |
| 53) | 5-[p-(CH$_3$)$_2$NC$_6$H$_4$N=CH—] |
| 54) | 5-C$_2$H$_5$OOC |
| 55) | 5-HOOC— |
| 56) | 4,5-(CH$_3$—)$_2$ |
| 57) | 4-CH$_3$-5-C$_2$H$_5$— |
| 58) | 4-C$_2$H$_5$-5-CH$_3$— |
| 59) | 4,5-(C$_2$H$_5$—)$_2$ |
| 60) | 4-(n-C$_3$H$_7$—)-5-CH$_3$— |
| 61) | 4-(n-C$_4$H$_9$—)-5-CH$_3$— |
| 62) | 4-CH$_3$-5-(t-C$_4$H$_9$—) |
| 63) | 4-(CH$_3$)$_3$CCH$_2$-5-(t-C$_4$H$_9$—) |
| 64) | 4-[(C$_2$H$_5$)$_2$NCH$_2$CH$_2$—]-5-CH$_3$.HClO$_4$ |
| 65) | 4-[(C$_2$H$_5$)$_2$NCH$_2$CH$_2$—]-5-CH$_3$.HCl |
| 66) | 4-C$_6$H$_4$CH$_2$-5-CH$_3$— |
| 67) | 4-CH$_3$-5-C$_6$H$_5$— |
| 68) | 4-C$_6$H$_5$-5-CH$_3$— |
| 69) | 4-C$_2$H$_5$-5-C$_6$H$_5$— |
| 70) | 4-CH$_3$-5-(p-CH$_3$C$_6$H$_4$—) |
| 71) | 4-CH$_3$-5-(p-ClC$_6$H$_4$—) |
| 72) | 4-CH$_3$-5-(p-BrC$_6$H$_4$—) |
| 73) | 4-CH$_3$-5-(p-IC$_6$H$_4$—) |
| 74) | 4-CH$_3$-5-(o-CH$_3$OC$_6$H$_4$—) |
| 75) | 4-CH$_3$-5-(p-CH$_3$OC$_6$H$_4$—) |
| 76) | 4-(p-CH$_3$OC$_6$H$_4$—)-5-CH$_3$— |
| 77) | 4-CH$_3$-5-[2,4-(CH$_3$)$_2$C$_6$H$_3$—] |
| 78) | 4-CH$_3$-5-[2,5-(CH$_3$)$_2$C$_6$H$_3$—] |
| 79) | 4-CH$_3$-5-[3,4-(CH$_3$)$_2$C$_6$H$_3$—] |
| 80) | 4-CH$_3$-5-(4-CH$_3$O-3-(CH$_3$C$_6$H$_3$—) |
| 81) | 4-CH$_3$-5-(2CH$_3$O-4-CH$_3$C$_6$H$_3$—) |
| 82) | 4-CH$_3$-5-(2-CH$_3$O-5-CH$_3$C$_6$H$_3$—) |
| 83) | 4-CH$_3$-5-(2-CH$_3$S-5-CH$_3$C$_6$H$_3$—) |
| 84) | 4-CH$_3$-5-(2-HO-3-CH$_3$OC$_6$H$_3$—) |
| 85) | 4-CH$_3$-5-[2,4-(CH$_3$O)$_2$C$_6$H$_3$—] |
| 86) | 4-CH$_3$-5-[2,5-(CH$_3$O)$_2$C$_6$H$_3$—] |
| 87) | 4-CH$_3$-5-[3,4-(CH$_3$O)$_2$C$_6$H$_3$—] |
| 88) | 4-CH$_3$-5-[2,4,6-(CH$_3$)$_3$C$_6$H$_2$—] |
| 89) | 4-(1-Naphthyl-)-5-CH$_3$— |
| 90) | 4-(1-Naphthyl-)-5-C$_2$H$_5$— |
| 91) | 4-CH$_3$-5-(2-CH$_3$O-1-naphthyl-) |
| 92) | 4-CH$_3$-5-(2-thienyl-) |
| 93) | 4-(2-Thienyl-)-5-CH$_3$— |
| 94) | 4-(5-CH$_3$-2-thienyl-)-5-CH$_3$— |
| 95) | 4-CH$_3$-5-(5-CH$_3$-2-thienyl-) |
| 96) | 4-C$_2$H$_5$-5-(5-CH$_3$-2-thienyl-) |
| 97) | 4-(5-C$_2$H$_5$-2-thienyl-)-5-CH$_3$— |
| 98) | 4-CH$_3$-5-(5-C$_2$H$_5$-2-thienyl-) |
| 99) | 4-C$_2$H$_5$-5-(5-C$_2$H$_5$-2-thienyl-) |
| 100) | 4-CH$_3$-5-[4,5-(CH$_3$)$_2$-2-thienyl-] |
| 101) | 4-CH$_3$-5-(3-pyridyl-) |
| 102) | 4-C$_2$H$_5$-5-(3-pyridyl-) |
| 103) | 4-n-C$_4$H$_9$-5-(3-pyridyl-) |
| 104) | 4-CH$_3$-3-(4-pyridyl-) |
| 105) | 4-C$_2$H$_5$-5-(4-pyridyl-) |
| 106) | 4-C$_2$H$_5$-5-(C$_6$H$_5$CH=CH—) |
| 107) | 4-CH$_3$-5-(p-CH$_3$OC$_6$H$_4$CH=CH—) |
| 108) | 4-C$_2$H$_5$-5-(p-CH$_3$OC$_6$H$_4$CH=CH—) |
| 109) | 4-(-n-C$_3$H$_7$—)-5-(p-CH$_3$OC$_6$H$_4$CH=CH—) |
| 110) | 4-C$_2$H$_5$-5-(2-furyl-CH=CH—) |
| 111) | 4-(n-C$_3$H$_7$—)-5-(2-furyl-CH=CH—) |
| 112) | 4-C$_6$H$_5$-5-C$_6$H$_5$CH$_2$— |
| 113) | 4-(C$_6$H$_5$CO—)-5-C$_6$H$_5$— |
| 114) | 4-(C$_6$H$_5$CS—)-5-C$_6$H$_5$— |
| 115) | 4,5-(C$_6$H$_5$—)$_2$ |
| 116) | 4-(p-CH$_3$OC$_6$H$_4$—)-5-C$_6$H$_5$— |
| 117) | 4-(p-HOC$_6$H$_4$—)-5-C$_6$H$_5$— |
| 118) | 4-(p-CH$_3$CO$_2$C$_6$H$_4$—)-5-C$_6$H$_5$— |
| 119) | 4-C$_6$H$_5$-5-(2-CH$_3$O-5-CH$_3$C$_6$H$_3$—) |
| 120) | 4,5-(p-CH$_3$OC$_6$H$_4$—)$_2$ |
| 121) | 4-[2,4-(CH$_3$O)$_2$C$_6$H$_3$— -5-C$_6$H$_5$—] |
| 122) | 4-(3-HO$_2$S-4-CH$_3$OC$_6$H$_3$—)-5-C$_6$H$_5$— |
| 123) | 4-(3-ClO$_2$S-4-CH$_3$OC$_6$H$_3$—)-5-C$_6$H$_5$— |
| 124) | 4-(3-C$_2$H$_5$O$_3$S-4-CH$_3$OC$_6$H$_3$—)-5-C$_6$H$_5$— |
| 125) | 4-(3-C$_6$H$_5$NHO$_2$S-4-CH$_3$OC$_6$H$_3$—)-5-C$_6$H$_5$— |
| 126) | 4-(3-CH$_3$CO-4-CH$_3$OC$_6$H$_3$—)-5-C$_6$H$_5$— |
| 127) | 4-(3-C$_2$H$_5$CO-4-CH$_3$OC$_6$H$_3$—)-5-C$_6$H$_5$— |
| 128) | 4-C$_6$H$_5$-5-(3-pyridyl-) |
| 129) | 4-C$_6$H$_5$-5-(4-pyridyl-) |
| 130) | 4-C$_6$H$_5$-5-(2-furyl-CH=CH—) |
| 131) | 4-CH$_3$-5-CH$_3$O$_2$C— |
| 132) | 4-CH$_3$O$_2$C-5-C$_6$H$_5$— |

TABLE I-continued

| | |
|---|---|
| 133) | 4-$C_2H_5O_2C$-5-$C_6H_5$— |
| 134) | 4-$C_6H_5$-5-$CH_3O_2C$— |
| 135) | 4-$CH_3$-5-[p-$(CH_3)_2NC_6H_4$N=CH—] |
| 136) | 4-$C_2H_5$-5-[p-$(CH_3)_2NC_6H_4$N=CH—] |
| 137) | 4-(n-$C_3H_7$—)-5-[p-$(CH_3)_2NC_6H_4$N=CH—] |
| 138) | 4-$C_6H_5$-5-[p-$(CH_3)_2$ $NC_6H_4$N=CH—] |
| 139) | 4-HS-5-$C_6H_5$— |
| 140) | 4-HS-5-(p-$CH_3OC_6H_4$—) |
| 141) | 4-$CH_3$S-5-$C_6H_5$— |
| 142) | 4-$CH_3$S-5-(p-$CH_3OC_6H_4$—) |
| 143) | 4-$CH_3COS$-5-$C_6H_5$— |
| 144) | 4-$CH_3COS$-5-(p-$CH_3OC_6H_4$—) |
| 145) | 4-$C_6H_5COS$-5-$C_6H_5$— |
| 146) | 4-$C_6H_5COS$-5-(p-$CH_3OC_6H_4$—) |
| 147) | 4-$CH_3O$-5-$C_6H_5$— |

1,2-dithiole-3-thiones can be converted to 1,2-dithiolium compounds by oxidizing 1,2-dithiole-3-thiones. Any convenient method oxidation can be employed.

The preferred method of preparation depends on the particular thione to be oxidized. For example, where the thione yields an unstable dithiolium compound, it is desirable to precipitate the dithiolium salt from solution so that it does not decompose. This is done by precipitating the thiolium as an insoluble salt so it will not be decomposed by further oxidation. For example, aryl thiones when converted to the corresponding dithiolium compounds are unstable to further oxidation but their decomposition can be prevented by precipitation from solution during oxidation as insoluble salts.

My application Ser. No. 79,709, filed Oct. 9, 1970, discloses that non-aryl substituted such as aliphatic dithiolethiones when converted to the corresponding dithiolium compounds yield stable compounds which are not subject to further oxidative decomposition. Therefore, it is not as important to precipitate such dithiolium compounds from solution as insoluble salts.

Application Ser. No. 79,709 further discloses that, in general, the aliphatic dithiolium compounds are also more water soluble than the aryl dithiolium compounds. For example, certain aliphatic dithiolium compounds are at least 75% water soluble in contracts to the less than 10% solubility of the aryl dithiolium compounds. Thus aliphatic dithiolium compounds are not only more soluble but are also more stable than the aryl compounds.

Application Ser. No. 79,709 further discloses that because of their high aqueous solubility and stability the aliphatic dithiolium compounds are particularly useful as corrosion inhibitors in aqueous and/or aerated and/or acidic systems.

A wide variety of oxidizing agents can be employed, as illustrated by the following:

1. aqueous solution of hydrogen peroxide
2. hydrogen peroxide and an organic or inorganic acid
3. barium permanganate
4. t-butyl-hydroperoxide
5. m-chloroperbenzoic acid
6. Caro's acid
7. Peracetic acid
8. Potassium persulfate
9. chromic anhydride
10. perchloric acid, etc.
11. Other oxidation agents can also be employed.

The choice of oxidizing agent will depend on the particular thione to be oxidized, economics, etc.

In general, the thione is oxidized in a suitable solvent at as low a temperature consistent with a reasonable reaction time so as to minimize side reactions. The particular reaction time will depend on the particular thione, the particular oxidizing agent, etc.

In practice reaction times of from 0.5 hours to 24 or more hours are employed; with hydrogen peroxides shorter time can be employed such as from about 1–2 hours. With milder oxidizing agents such as organic peroxides longer times may be employed such as 24 hours with chloroperbenzoic acid.

Any solvent that does not interfere with the reactants and products can be employed for example; water, methanol, ethanol, 1-propanol, butanol, acetone, dimethyl sulfamide, dimethyl formamide, ether tetrahydrofuran, chloroform, carbon tetrachloride, etc.

In general, room temperature or lower is preferably employed to reduce side reactions. Higher temperatures may be employed in oxidizing certain thiones such as about 50°C. or higher in certain instances.

Although S.N. 79,709 discloses the oxidation of thiones, dithiolium compounds can be prepared by other methods such as for example by those described in "Advances in Heterocyclic Chemistry," Katritzby, et al., Vol. 7, 1966, published by Academic Press, pp 39–151, which is incorporated herein as if part thereof.

The following Examples are presented by way of illustration and not of limitation.

EXAMPLE 1B 3-t-Butyl-4-neopentyl-1,2-dithiolium hydrogen sulfate

In a 2 liter four necked round-bottom flask equipped with a mechanical stirrer, a thermometer, a reflux condenser and an addition funnel was placed a mixture of 260 grams of 4-neopentyl-5-t-butyl-1,2-dithiole-3-thione and 500 cc of glacial acetic acid. The mixture was cooled to 15°C. and 258 grams of 305 hydrogen peroxide was added at such a rate that a reaction temperature of 15°–25°C. was maintained (two hours). After the addition was completed, the mixture was stirred for an additional two hours at room temperature. The solvents were distilled off under diminished pressure. The remaining solid was washed with acetone and filtered to yield 258 grams (80% of theory) of 3-t-butyl-4-neopentyl-1,2-dithiolium hydrogen sulfate as a light yellow solid; m.p. 189°–190°C; u.v. $\lambda$ $^{H_2O}_{max}$. (E) 254 m$\mu$ (5,000) and 306 m$\mu$ (6,800); nmr (solvent $D_2O$) $\tau$ in ppm, internal standard t.m.s., −0.03 (s., 1H), 6.74 (s., 2H), 8.22 (s., 9H) and 8.88 (s., 9H).

Anal. Calced. for $C_{12}Hhd 22O_4S_3$: C, 44.14; H, 6.74; S, 29.43. Found: C, 43.98; H, 6.82; S, 29.8.

EXAMPLE 2B 3-t-Butyl-4-neopentyl-1,2-dithiolium perchlorate $HSO_4^- \longrightarrow ClO_4^-)$.

To a solution of 5 grams of 3-t-butyl-4-neopentyl-1,2-dithiolium hydrogen sulfate in 5 grams of distilled water was added 4 cc of 70% perchloric acid. The white solid which precipitated was filtered and dried to yield 5 grams (100%) of material, m.p. 157°–158°C; u.v. $\lambda\ ^{EtOH}_{max}$ (E) 254 m$\mu$ (4,780) and 307 m$\mu$ (5,010).

Anal. Calced. for $C_{12}H_{21}S_2ClO_4$: S, 19.5. Found: S, 19.4.

EXAMPLE 3B 3-t-Butyl-4-neopentyl-1,2-dithiolium hydrogen sulfate

The product was prepared in 80 percent of the theoretical yield according to a procedure identical as in Example 1B, with the exception that instead of acetic acid as the solvent, a mixture of 50 g of acetic acid and 450 g of isopropanol as the solvent was employed.

EXAMPLE 4B 3-t-Butyl-4-neopentyl-1,2-dithiolium hydrogen sulfate

To a sample of 5.2 grams of 4-neopentyl-5-t-butyl-1,2-dithiole-3-thione dissolved in 100 grams of chloroform was added a solution of 12.2 grams of m-chloroperbenzoic acid (85%) in 200 grams of chloroform. The mixture was allowed to stand for 24 hours at room temperature. The chloroform solution was evaporated under diminished pressure and the remaining solid extracted with 100 cc of distilled water. The aqueous solution was distilled under diminished pressure to yield 4.8 grams (73 percent of theory) of Example 1B.

EXAMPLE 5B 4-phenyl-1,2-dithiolium hydrogen sulfate

This product was prepared in 80 percent yield from 4-phenyl-1,2-dithiole-3-thione according to the procedure described in Example 4B. Bright yellow solid m.p. 230°–232°C. (dec.); u.v. $\lambda\ ^{H_2O}_{max.}$ (E) 242 m$\mu$ (15,400) and 345 m$\mu$ (1,700),nmr (solvent $D_2O$) in ppm, internal standard t.m.s., −0.06 (s., 2H) and 2.05–2.51 (m., 5H).

Anal. Calced. for $C_9H_8O_4S_3$: C, 39.1; H, 2.9; S, 34.8. Found: C, 38.8; H, 3.1; S, 34.9.

EXAMPLE 6B 3-(p-methoxy phenyl) - 1,2 thiolium hydrogen sulfate

The desired product was obtained in a 40% yield, according to the procedure described in Example 1B, as an orange solid, m.p. 195°–196°C. (dec.), after crystallization from ethanol; u.v. $\lambda\ ^{H_2O}_{max.}$ (E) 244 m$\mu$ (7,100) and 411 m$\mu$ (23,300).

Anal. Calced. for $C_{10}H_{10}O_5S_3$: C, 39.2; H, 3.3; S, 31.4. Found: C, 39.1; H, 3.1; S, 31.2.

The formulae of the above dithiolium compounds are presented in the following Table.

TABLE II

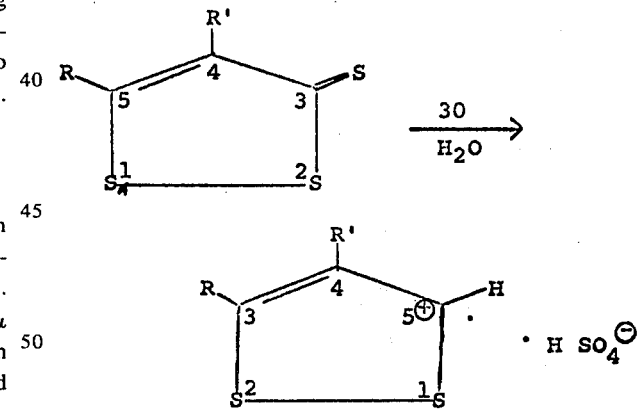

| Ex. | R (3) | R' (4) | X |
|---|---|---|---|
| 1B | $CH_3-\underset{CH_3}{\overset{CH_3}{C}}-$ | $CH_3-\underset{CH_3}{\overset{CH_3}{C}}-CH_2-$ | $HSO_4$ |
| 2B | $CH_3-\underset{CH_3}{\overset{CH_3}{C}}-$ | $CH_3-\underset{CH_3}{\overset{CH_3}{C}}-CH_2-$ | $ClO_4$ |
| 3B | Same as Example 1 | | |
| 4B | Same as Example 1 | | |
| 5B | H | phenyl | $HSO_4$ |
| 6B | $CH_3O-$phenyl- | H | $HSO_4$ |

The reaction may be summarized as follows:

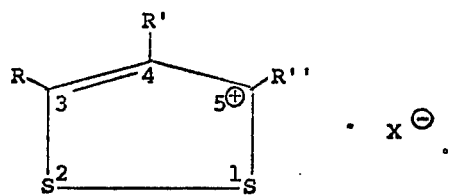

The anion employed will depend on the properties desired for example solubility, insolubility, partial solubility. Example of anions include sulfates, bisulfates, sulfites, bisulfites, halides, i.e., Cl, Br, I, F, etc., phosphates, phosphites, etc., chlorates, etc. In addition to employing the salts, quaternaries can be employed so that the hydrogen in the 5 position R'' is for example alkyl, aryl, etc.

Any suitable quaternizing agent may be employed, for example,

Polyfunctional quaternaries may also be formed, for example

1. alkyl halides such as methyl iodide, butyl iodide, butyl bromide, etc.
2. Sulfuric acid and derivatives $H_2SO_4$, $R_2SO_4$ where R is alkyl, etc., methyl, ethyl, etc. for example $(Me)_2SO_4$
3. Alkyl thioureas such as methyl thiourea, etc.
4. Sulfonate esters, for example

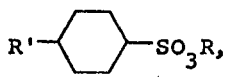

where R is alkyl such as methyl, etc., and R is hydrogen, alkyl, etc., for example, methyl p-toluene sulfonates.

5. Alkyl phosphates, e.g. $(MeOO)_3PO$, $(EtO)_3PO$, etc.

It is to be noted that where the anion is polyfunctional, such as difunctional, 2 moles of the dithiolium would be coupled with one mole of the anion, for example

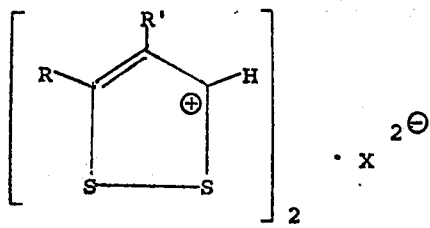

such as where X is sulfate, a dicarboxylic acid such as phthalic acid, etc., for example

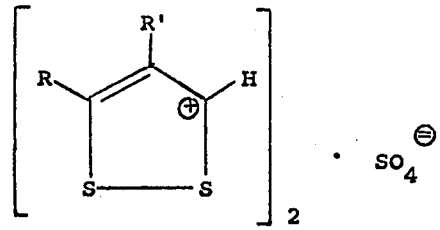

etc.

such as where A is alkylene,

—$CH_2$—⟨ ⟩—$CH_2$—,

—$(CH_2CH_2)_2O$, —$CH_2$—$CH=CH$—$CH_2$—, etc.

I have now discovered a process of reacting the dithiolium compounds described herein with phosphite esters under basic conditions to form thiophosphates of the formula

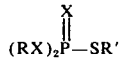

where X is O or S, R is a hydrocarbon or a substituted hydrocarbon group such as alkyl, aryl, cycloalkyl, aralkyl, alkaryl, etc., and R' is a 3-thione-propene-1 or a substituted 3-thione-propene-1 group. I have also discovered that the process can be reversed to the original dithionium compound by reacting the thiophosphate product under acid conditions.

The overall reaction can be summarized by the following equations where B is a base. In the following equations the phosphite ester can also be a thiophosphite, or a mixed oxygenthiophosphite, i.e.,

where X is O or S. Thus all X's may be oxygen or sulfur or both oxygen and sulfur. Corresponding thiophosphates will be formed.

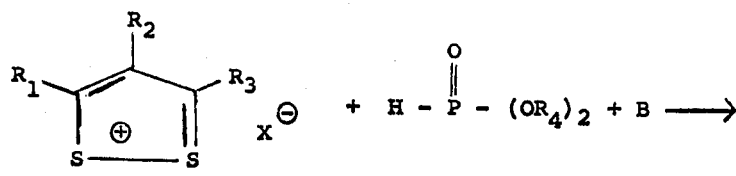

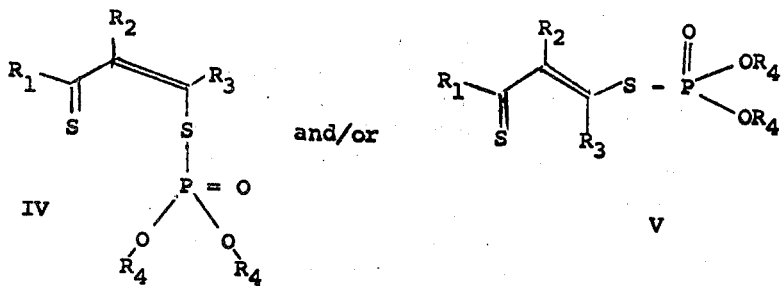

and/or

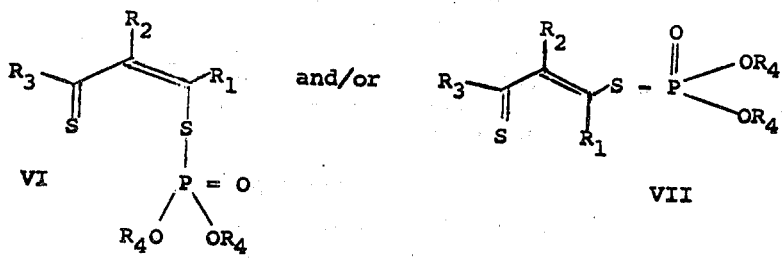

+ B⊕HX⊖

VIII

The reversed reaction is given by the equation:

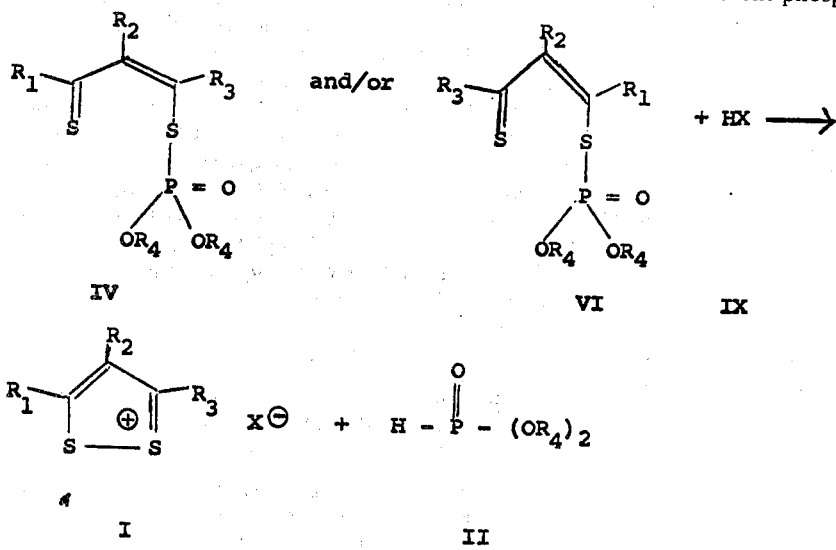

The products obtained are IV and/or V and/or VI and/or VII.

Since the starting material can be represented by the two extreme resonance structures.

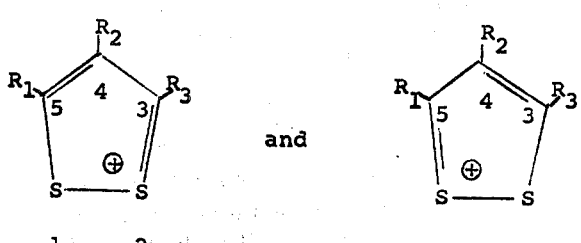

two different phosphor-sulfur bonds can be formed if $R_1 \neq R_3$ and since each product formed can exist as two isomers a total of four products is possible.

The formation of IV, V, VI and VII will depend upon the nature of $R_1$, $R_2$, and $R_3$ groups and of the phosphite used.

The dithiolium compounds described herein as well as others can be reacted under basic conditions with phosphites to form the monothiophosphates.

In general the reaction is carried out by reacting one mole of the dithiolium compound wiht at least 1 mole of phosphite at ambient temperature, such as from about $-10°$ to $60°C$, but preferably at about room temperature, i.e., from $0°$ to about $30°C$.

The phosphites employed in this invention are of the formula

where R is an alcohol moiety, for example, alkyl, aryl, cycloalkyl, aralkyl, alkaryl, and substituted derivatives thereof, but preferably where R is alkyl, for example, $C_1$ to $C_{18}$ or higher, and most preferably lower alkyl, i.e., $C_1$ to $C_8$.

In addition, the oxygen phosphites, corresponding thiophosphite or mixed oxygen thiophosphites can be employed, for example, of the general formula

where X is oxygen or sulfur, for example,

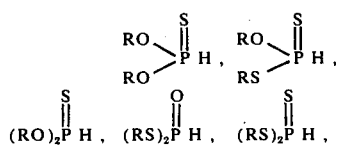

etc.

Any basic material capable of promoting the reaction can be employed. These include alkali metal and alkaline earth metal hydroxides, oxides, alkoxides, and also salts of these metals with weak, inorganic and organic acids, for example, those derived from Group IA and IIA of the periodic table.

As examples of the alkali metal and alkaline earth metal hydroxides, there may be mentioned sodium hydroxide, potassium hydroxide, lithium hydroxide, calcium hydroxide, barium hydroxide, strontium hydroxide, and magnesium hydroxide. The alkoxides are represented by sodium n-butoxide, and the corresponding potassium lithium, calcium, strontium, barium and magnesium alcoholates.

The preferred basic material comprises amines. Although a wide variety of amines can be employed such as primary, secondary, tertiary, mono and polyamines, in order to reduce side reactions tertiary amines are employed, preferably volatile tertiary monoamines that can be easily removed on completion of the reaction, for example tertiary amines of the formula

where the R's, which may be the same or different, are hydrocarbon, preferably alkyl and most preferably lower alkyl, for example, where the R's are methyl, ethyl, propyl, butyl, pentyl, hexyl, heptyl, etc., where the alkyls are straight chained, branched, etc.

Ammonia can also be employed, i.e., where the R's are hydrogen.

In general, sufficient base is employed to remove the anion so as to render the system basic, i.e., at least one equivalent of base per mole of dithiolium compound.

The anion $X^-$ may be stated herein in relation to the dithiolium compound, for example halides (Cl, Br, I, F) chlorates, carboxylates, such as derived from aliphatic acids, for example acetates, propionates, etc., aromatic acids, for example benzoates, salicylates, phthalates, etc., phosphates, sulfates, sulfonates, etc.

The thiophosphate can be reconverted to the dithiolium compound by adding a sufficient amount of an acidic material to render it acidic, thus reverting it to the cationic form. To achieve this at least one equivalent of acid is added per mole of dithiole. The acidic material can be organic or inorganic, for example, hydrohalic acids such as HCl, HBr, etc., sulfuric, phosphoric, sulfonic acids, etc; organic acids such as the alkyl, aryl, cycloalkyl, alkaryl, aralkyl, heterocyclic, etc., carboxylic acids, for example acetic, propionic, butyric, etc., fatty acids such as stearic, oleic, palmitic, etc., acids, benzoic, phthalic, etc., acids.

The following examples are presented for purposes of illustration and not limitation.

EXAMPLE 1C

O,O'-Dimethyl-S-(2-Neopentyl-4,4-dimethyl-3-thione-pentene-1) monothiophosphate

To a mixture of 16.4 grams of 3-tertiary-butyl-4-neopentyl-1,2 dithiolium perchlorate (Ex. 2B) and 19.0 grams of the dimethylphosphite was added 7.3 grams of triethylamine. After the addition of triethylamine was completed, there was added 100cc of ether and 50 cc of water. The etheral layer wa separated and washed several times with water. After the ether solution was dried over anhydrous magnesium sulfate, the ether was distilled off under diminished pressure. There was isolated 16.5 grams (97% of theory) of O,O'-dimethyl-S-(2-neopentyl-4, 4-dimethyl-3-thione-pentene-1) monothiophosphate as a red-purple solid, melting point 69°–71°C; n.m.r. (solvent $CCl_4$), $\tau$ in ppm, 4.13, 1 H doublet (J = 9 cps, vinyl); 6.31, 6 H doublet (J = 13 cps, methoxy); 7.66, 2 H singlet ($CH_2$ neopentyl); 8.63, 9 H singlet (t-butyl), and 9.08, 9 H singlet (t-butyl).

Anal. Calculated for $C_{14}H_{27}O_3PS_2$ : P, 9.17; S, 19.0. Found: P, 9.05, S, 20.1.

EXAMPLE 2C

O,O'-Dimethyl-S-(2-Neopentyl-4,4-dimethyl-3-thione-pentene-1) monothiophosphate

A mixture of 15 grams of 3-tertiary-butyl-4-neopentyl-1,2 dithiolium hydrogen sulfate (Ex. 1B) and 15 grams of dimethyl phosphite dissolved in 50 grams of water was treated slowly with 10 grams of 29% ammonium hydroxide solution. The product which precipitated was filtered off and washed with water. After drying in vacuo, there was isolated 13.5 grams of O,O'-dimethyl-S-(2-neopentyl-4,4-dimethyl-3-thione-pentene-1) monothiophosphate (86 percent of theory) in all respects identical to the product isolated as described in Example 1C.

EXAMPLE 3C

O,O'Diethyl-S-(2-Neopentyl-4,4-dimethyl-3-thione-pentene-1) monothiophosphate

A mixture of 6.0 grams of 3-tertiarybutyl-4-neopentyl-1,2 dithiolium perchlorate (Ex. 2B) and 3.73 grams of diethylphosphite in 30 cc of ether was treated with 2.73 grams of triethylamine. The ethereal solution was extracted several times with water. After the ethereal solution was dried over anhydrous magnesium sulfate, the ether was distilled off under diminished pressure. There was isolated 6.36 grams of O,O'-diethyl-S-(2-neopentyl-4,4-dimethyl-3-thione-pentene-1)monothiophosphate (96 percent of theory) as a purple liquid; n.m.r. (solvent CCl$_4$), $\tau$ in ppm, 4.03, 1 H doublet (J = 9 cps, vinyl); 5.88, 4 H multiplet (ethoxy); 7.61, 2 H singlet (neopentyl): 8.59 9 H singlet (tertiaryutyl); 86.67 6 H triplet (J = 7.5 cps, ethoxyl); and 9.04, 9 H singlet (tertiarybutyl).

Anal. Calculated for C$_{16}$H$_{31}$O$_3$PS$_2$ P P, 8.45; S, 17.5. Found : P, 8.19, S, 18.3.

EXAMPLE 4C

O,O'Diisopropyl-S-(2-Neopentyl-4,4-dimethyl-3-thione-pentene-1) monothiophosphate In a fashion as described in Example 3C, there was reacted 6.0 grams of 3-tertiary butyl-4-neopentyl-1,2 dithiolium perchlorate (Ex. 2B), 4.49 grams of diisopropyl phosphite and 2.73 grams of triethylamine. The reaction mixture was worked up in a manner as described in Example 3C to yield 7.1 grams (100 percent of theory) of O,O'-diisopropyl-S-(2-neopentyl-4,4-dimethyl-3-thione-pentene-1) monothiophosphate as a purple liquid; n.m.r. (solvent CCl$_4$), $\tau$ in ppm, 4.00, 1 H doublet (J = 10 cps, vinyl); 5.30, 2 H multiplet (isopropoxy); 7.60, 2 H singlet (neopentyl); 8.59, 9 H singlet (tertiarybutyl); 8.67, 12 H doublet (isopropoxy); and 9.03, 9 H singlet (tertiarybutyl).

Anal. Calculated for C$_{13}$H$_{35}$O$_3$Ps$_2$ : P, 7.90 Found: P, 8.10

EXAMPLE 5C

O,O'-Di-n-butyl-S-(2-Neopentyl-4,4-dimethyl-3-thione-pentene-1) monothiophosphate As described in Example 3C, there as reacted 6.0 grams of 3-tertiarybutyl-4-neopentyl-1,2-dithiolium perchlorate (Ex. 2B), 5.24 grams of di-n-butyl phosphite and 2.73 grams of triethylamine. There was isolated 7.6 grams (100% of theory) of O,O'-di-n-butyl-S-(2-neopentyl-4,4-dimethyl-3-thione-pentene-1) monothiophosphate as a purple liquid; n.m.r. (solvent CCl$_4$), $\tau$ in ppm, 4.03, 1 H doublet (J = 10 cps, vinyl); 5.92, 4 H multiplet (n-butyl); 7.62, 2 H singlet (neopentyl); 8.12–9.30, 14 H multiplet (n-butyl); 8.59 9 H singlet (tertiarybutyl); and 9.05, 9 H singlet (t-butyl).

EXAMPLE 6C

O,O'-Diphenyl-S-(2-Neopentyl-4,4-dimethyl-3-thione-pentene-1) monothiophosphate

To a mixture of 10.0 grams of 3-tertiarybutyl-4-neopentyl-1,2-dithiolium hydrogen sulfate (Ex. 1A) and 4.7 grams of diphenyl phosphite in 30 cc of ether was added 2.0 grams of triethylamine. The mixture was stirred for 10 minutes and filtered The ether was distilled off under diminished pressure to yield 7.2 grams (78 percent of theory) of the substituted monothiophosphate as a viscous purple liquid. Upon standing for one day the product changed into a pink solid, melting point 75°–80°C. Crystallization from methanol yielded O,O'-diphenyl-S-(2-neopentyl-4,4-dimethyl-3-thione-pentene-1) monothiophosphate as yellow needles; melting point 97°–98°C; n.m.r. (solvent CCl$_4$), $\tau$ in ppm, 2.52–2.83, 10 H multiplet (phenyl); 5.27, 1 H doublet (J 32 13.5 cps., vinyl); 7.30, 2 H multiplet (neopentyl); 8.81, 9 H singlet (tertiarybutyl); and 8.96, 9 H singlet (tertiarybutyl).

Anal. Calculated for C$_{24}$H$_{31}$O$_3$PS$_2$ : P, 6.75; S, 13.85. Found : P, 6.54; S, 13.80.

EXAMPLE 7C 3-tertiarybutyl-4-Neopentyl-1,2-Dithiolium Perchlorate

A sample of 1.5 grams of O,O'-dimethyl-S-(2-neopentyl-4, 4-dimethyl-3-thione-pentene-1) monothiophosphate was dissolved in 15 grams of methanol. To the solution was added 2.3 grams of 70% perchloric acid and 45 grams of water. The precipitate was filtered off and dried. The product was in all respects identical to 3-tertiarybutyl-4-neopentyl-1,2 dithiolium perchlorate as described in Ex. 2B.

The corresponding product was obtained by treating O,O'-diethyl-S-(2-neopentyl-4,4-dimethyl-3-thione-pentene-1) monothiophosphate with 70% perchloric acid.

EXAMPLE 8C

A sample of 0.6 grams of O,O'-diphenyl-S-(2-neopentyl-4, 4-dimethyl-3-thione-pentene-1) monothiophosphate dissolved in 19 grams of methanol was treated with 0.9 grams of 70% perchloric acid. To the mixture was added 18 grams of water. The precipitate was filtered off and dried. There was isolated 0.6 grams of the corresponding dithiolium compound of Ex. 2B.

The formulae of the monothiophosphates formed in the above examples are in the following Table.

Table III

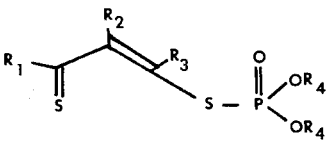

| Ex. | R$_1$ | R$_2$ | R$_3$ | R$_4$ |
|---|---|---|---|---|
| 1C | tert-Butyl | Neopentyl | H | CH$_3$ |
| 2C | tert-Butyl | Neopentyl | H | CH$_3$ |
| 3C | tert-Butyl | Neopentyl | H | C$_2$H$_5$ |
| 4C | tert-Butyl | Neopentyl | H | iso-C$_3$H$_7$ |
| 5C | tert-Butyl | Neopentyl | H | n-C$_4$H$_9$ |
| 6C | tert-Butyl | Neopentyl | H | Phenyl |

Other monothiophosphates similarly prepared are presented in the following Table.

Table IV

| Ex. No. | dithiolium starting material | phosphite | Product |
| --- | --- | --- | --- |
| 9C | 3,5 Diphenyl 1,2-dithiolium perchlorate | dimethyl phosphite | O,O'-Dimethyl-S-(1,3 diphenyl-3-thione-propene-1) monothiophosphate |
| 10C | 3,5 Diphenyl 1,2 dithiolium perchlorate | diphenyl phosphite | O,O'-Diphenyl-S-(1,3 diphenyl-3-thione-propene-1) monothiophosphate |
| 11C | 3-Phenyl-4-methyl 1,2-dithiolium perchlorate | dimethyl phosphite | O,O'-Dimethyl-S-(2-methyl-3-phenyl-3-thione-propene-1) monothiophosphate |

Since the thiophosphates of this invention are more soluble in organic systems than the corresponding dithiolium compounds, they can be added to the organic phase of the systems in greater concentrations than the dithiolium compounds. When the organic phase is brought into contact with the acidic aqueous phase, the thiophosphate is converted to the dithiolium compound at the interphase and extracted into the aqueous phase in which it is more soluble. In this way there is a gradual and continuous transfer from one phase to another as it is converted to its anti-corrosive form. Thus, the oil solubility of the thiophosphate facilitates handling in oil systems and acid convertibility with subsequent enhanced water solubility of the product transports the corrosion inhibitor to the aqueous phase. In this way the corrosion inhibitor is stored in the organic phase until ready for use where it gradually migrates to the aqueous acidic corrosive system as required.

In addition, an organic solution or suspension of the thiophosphate can be placed in contact with the metal, as a liquid, grease, etc., and as acid fumes or aqueous acid vapors contact the system, the thiophosphate converts to the dithiolium compound which acts as a corrosion inhibitor as required.

USE IN FLUIDS FOR DRILLING WELLS

This phase of the invention relates to the use of the compounds of this invention as corrosion inhibitors in producing an improved drilling fluid useful in drilling oil and gas wells.

Fluids commonly used for the drilling of oil and gas wells are of two general types: water-base drilling fluids comprising, for example, a clay suspended in water, and oilbase drilling fluids comprising, for example, a clay or calcium carbonate suspended in mineral oil.

A third type of drilling fluid which has recently been developed is one of oil-in-water or water-in-oil emulsion, for example, emulsions of mineral oil in water or water in mineral oil formed by means of emulsifiers such as sulfuric acid; Turkey-red oil; soaps of fatty acids, for example, sodium oleate; emulsoid colloids, for example, starch, sodium alginate, etc. Varying amounts of finely divided clay, silica, calcium carbonate, blown asphalt and other materials may be added to these emulsions to improve their properties and control their weight.

I have now discovered that the compositions of this invention can be employed as a corrosion inhibitor in drilling fluids.

USE IN AIR DRILLING

It has long been conventional practice in drilling deep bore holes to circulate a drilling mud down through the drill stem and up through the bore hole between the wall of the bore hole and the drill stem for the removal of chips or cuttings from the bore hole and to provide support for the wall of the bore hole. More recently, in the filling of holes in which wall support provided by drilling mud is not employed, drilling has been carried out with the use of air for chip removal. Such drilling is not only normally faster than mud drilling, but is indispensable in areas where the supply of water is limited or when drilling through cavernous formations into which the drilling mud flows and becomes lost.

The increasing popularity of air or gas drilling has come about not only because this method of drilling is frequently faster, as noted above, but for the additional reasons that the drill bits last longer, the provision and handling of water under wide ranges of temperature conditions is avoided, boring samples are easily observed when they are not mixed with mud, and there is no loss involved as in the case of mud drilling when drilling through cavernous formations. Furthermore, prompt removal of water entering the hole maintains a dry hole and the likelihood of wall collapse is thereby reduced.

In a typical air drilling operation there may be provided, for example, an up-flow of air in the bore hole having a velocity of the order of 3,000 feet per minute. This flow of air upwardly through the bore hole, which is produced by air pumped downwardly through the drill stem, provides adequate removal of cuttings. The air is delivered to the drill stem at pressures of 20 to 60 lbs. per square inch and for dewatering or for breaking obstructions, as will be hereinafter described, the pressures may be increased to 180 to 200 lbs. or more per square inch.

Air drilling operations are frequently hampered by the inflow of water into the bore hole when the drill bit is penetrating a water bearing stratum or when the bore hole has passed through a water bearing stratum that has not been cased. Normally, if drilling proceeds uninterruptedly both before and during penetration into a water bearing stratum, the flow of air is sufficient to blow the water out of the bore hole along with the cuttings and drilling dirt. There are, however, two major problems encountered in air drilling when water is entering the bore hole. The first problem occurs when there is a small inflow of water sufficient to cause a dampening of the cuttings which, under certain conditions, will then ball-up, clogging and sometimes jamming the drill bit. The second problem is encountered when there is a substantial amount of water remaining in the bottom of the bore hole during drilling causing a sloughing of the side wall of the bore hole. This latter condition may arise even though the water entering the bore hole is being blown out of the hole as fast as it enters. If there is a substantial inflow of water or if there is a substantial flow of water past a region of the bore hole susceptible to this condition, the water passing that region of the bore hole may cause a sloughing of the side wall.

The addition of foam forming materials to the air flow when air drilling is employed in conjunction with sufficient water to provide foaming gives rise to numerous advantages in drilling operations. The water may be introduced either through a water bearing stratum being penetrated by the drill bit or, alternatively, if the hole is dry, water may be introduced from the surface of the earth through the drill stem in conjunction with the delivery of compressed air and foam forming material through the drill stem to the drill bit. In either case the water may be said to be existing in the bore hole, and drilling operations are described in U.S. Pat. No. 3,130,798.

The amount of the compositions of the invention to be employed as a corrosion inhibitor can vary widely depending upon particular compounds, the particular system, the amounts of oxygen present, etc. I may employ concentrations of from about 0.5 to 5,000 p.p.m., such as from about 4 to 4,000 p.p.m., for example from about 20 to 2,000 p.p.m., but preferably from about 100 to 1,000 p.p.m. The optimum amount, to be determined in each instance, which will depend on function and economics, can be lesser or greater than the above amounts under proper conditions.

USE IN BRINES

This phase of the invention relates to the prevention of corrosion in systems containing a corrosive aqueous medium, and most particularly in systems containing brines.

More particularly, this invention relates to the prevention of corrosion in the secondary recovery of petroleum by water flooding and in the disposal of waste water and brine from oil and gas wells. Still more particularly, this invention relates to a process of preventing corrosion in water flooding and in the disposal of waste water and brine from oil and gas wells which is characterized by injecting into an underground formation an aqueous solution containing minor amounts of compositions of this invention, in sufficient amounts to prevent the corrosion of metals employed in such operation. This invention also relates to corrosion inhibited brine solutions of these compounds.

When an oil well ceases to flow by the natural pressure in the formation and/or substantial quantitites of oil can no longer be obtained by the usual pumping methods, various processes are sometimes used for the treatment of the oil-bearing formation in order to increase the flow of the oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well." The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system."

Because of the corrosive nature of oil field brines, to economically produce oil by water flooding, it is necessary to prevent or reduce corrosion since corrosion increases the cost thereof by making it necessary to repair and replace such equipment at frequent intervals.

I have now discovered a method of preventing corrosion in systems containing a corrosive aqueous media, and most particularly in systems containing brines, which is characterized by employing the compositions of this invention.

I have also discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation the compositions of this invention.

This phase of the invention then is particularly concerned with preventing corrosion in a water flooding process characterized by the flooding medium containing an aqueous or an oil field brine solution of these compounds.

In many oil fields large volumes of water are produced and must be disposed of where water flooding operations are not in use or where water flooding operations cannot handle the amount of produced water. Most states have laws restricting pollution of streams and land with produced waters, and oil producers must then find some method of disposing of the waste produced salt water. In many instances, therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compositions of this invention can also be used in such water disposal wells thus providing a simple and economical method of solving the corrosion problems encountered in disposing of unwanted water.

Water flood and waste disposal operations are too well known to require further elaboration. In essence, in the present process, the flooding operation is effected in the conventional manner except that the flooding medium contains a minor amount of the compound of this invention, sufficient to prevent corrosion, in concentrations of about 10 p.p.m. to 10,000 p.p.m., or more, for example, about 50 to 5,000 p.p.m., but preferably about 15 to 1,500 p.p.m. The upper limiting amount of the compounds is determined by economic considerations. Since the success of a water flooding operation manifestly depends upon its total cost being less than the value of the additional oil recovered from the oil reservoir, it is quite important to use as little as possible of these compounds consistent with optimum corrosion inhibition. Optimum performance is generally obtained employing about 1,000 p.p.m. Since these compounds are themselves inexpensive and are used in low concentrations, they enhance the success of a flood operation by lowering the cost thereof.

In addition, these compounds are not sensitive to oxygen content of the water and these are effective corrosion inhibitors in both open water flooding systems and closed water flooding systems.

While the flooding medium employed in accordance with the present invention contains water or oil field brine and the compounds, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc., and in conjunction with other secondary recovery methods.

Use in Acid Systems

The compounds of this invention can also be employed as corrosion inhibitors for acid systems, for example as illustrated by the pickling of ferrous methods, the treatment of calcareous earth formations, etc., as described in the following sections.

Use As Pickling Inhibitors

This phase of the invention relates to pickling. More particularly, the invention is directed to a pickling composition and to a method of pickling ferrous metal. The term "ferrous metal" as used herein refers to iron, iron alloys and steel.

To prepare ferrous metal sheet, strip, etc., for subsequent processing, it is frequently desirable to remove oxide coating, formed during manufacturing, from the surface. The presence of oxide coating, referred to as "scale" is objectionable when the material is to undergo subsequent processing. Thus, for example, oxide scale must be removed and a clean surface provided if satisfactory results are to be obtained from hot rolled sheet and strip in any operation involving deformation of the product. Similarly, steel prepared for drawing must possess a clean surface and removal of the oxide scale therefrom is essential since the scale tends to shorten drawing-die life as well as destroy the surface smoothness of the finished product. Oxide removal from sheet or strip is also necessary prior to coating operations to permit proper alloying or adherence of the coating to the ferrous metal strip or sheet. Prior to cold reduction, it is necessary that the oxide formed during hot rolling be completely removed to preclude surface irregularities and enable uniform reduction of the work.

The chemical process used to remove oxide from metal surfaces, is referred to as "pickling." Typical pickling processes involve the use of aqueous acid solutions, usually inorganic acids, into which the metal article is immersed. The acid solution reacts with the oxides to form water and a salt of the acid. A common problem in this process is "overpickling" which is a condition resulting when the ferrous metal remains in the pickling solution after the oxide scale is removed from the surface and the pickling solution reacts with the ferrous base metal. An additional difficulty in pickling results from the liberated hydrogen being absorbed by the base metal and causing hydrogen embrittlement. To overcome the aforementioned problems in pickling, it has been customary to add corrosion inhibitors to the pickling solution.

The present invention avoids the above-described problems in pickling ferrous metal articles and provides a pickling composition which minimizes corrosion, overpickling and hydrogen embrittlement. Thus the pickling inhibitors described herein not only prevent excessive dissolution of the ferrous base metal but effectively limit the amount of hydrogen absorption thereby during pickling. According to the invention, a pickling composition for ferrous metal is provided which comprises a pickling acid such as sulfuric or hydrochloric acid and a small but effective amount of the dithiol thione compound of this invention, for example at least about 5 p.p.m., such as from about 100 to 5,000 p.p.m., but preferably from about 500 to 1,500 p.p.m.

Ferrous metal articles are pickled by contacting the surface (usually by immersion in the pickling solution) with a pickling composition as described to remove oxide from their surface with minimum dissolution and hydrogen embrittlement thereof and then washing the ferrous metal to remove the pickling composition therefrom.

Use in Acidizing Earth Formations

The compositions of this invention can also be used as corrosion inhibitors in acidizing media employed in the treatment of deep wells to reverse the production of petroleum or gas therefrom and more particularly to an improved method of acidizing a calcareous or magnesium oil-bearing formation.

It is well known that production of petroleum or gas from a limestone, dolomite, or other calcareous-magnesian formation can be stimulated by introducing an acid into the producing well and forcing it into the oil or gas bearing formation. The treating acid, commonly a mineral acid such as HC1, is capable of forming water soluble salts upon contact with the formation and is effective to increase the permeability thereof and augment the flow of petroleum to the producing well.

The corrosion inhibitors were evaluated using sand blasted 1020 mild steel coupons monitored by a polarization resistance meter, a Pair instrument described in U.S. Pat. No. 3,406,101.

The acid was placed in a beaker and the coupons placed in the acid. Corrosion rates were measured at various time intervals and percent protection calculated in the usual manner as follows:

$$\text{Percent protection} = \frac{R_1 - R_2}{R_1} \times 100$$

where
$R_1$ is corrosion rate without inhibitor
$R_2$ is corrosion in presence of inhibitor.
The utility of the compositions of this invention is illustrated in the following Table.

Use as Corrosion Inhibitors In Highly Acid Systems

Table V

| H₂SO₄ 180 g per liter | | | |
|---|---|---|---|
| Fe⁺⁺ as FeSO₄ 10 g per liter | | | |
| Fe⁺⁺ as Fe(SO₄)₃ 10 g per liter | | | |
| Inhibitor concentration 1,000 p.p.m. | | | |
| Product of Example No. | Time | Temp. °F | % protection |
| 1C | 24 | 200 | 98 |
| 1C | 48 | 200 | 98 |
| 1C | 72 | 200 | 98 |
| 1C | 96 | 200 | 98 |
| 3C | 1 | 74 | 97 |
| 5C | 1 | 74 | 99 |
| 5C | 17 | 74 | 99 |

Table VI

| HCl 100 g per liter | | | |
|---|---|---|---|
| Fe⁺⁺⁺ as FeCl₂ 100 g per liter | | | |
| Inhibitor concentration 1,000 p.p.m. | | | |
| Product of Example No. | Time | Temp. °F | % Protection |
| 1C | 24 | 175 | 96 |
| 1C | 48 | 175 | 95 |
| 4C | 1 | 74 | 97 |
| 4C | 18 | 74 | 98 |

An important aspect of pickling inhibitors is that they should remain effective in presence of dissolved ferrous ions (from dissolution of the oxide scale). The continued effectiveness of the present compositions is illustrated in the above table.

The compositions of this invention may also be added to other aqueous and/or oxygenated systems such as steam generating systems, water circulating systems such as in cooling towers, in automobile radiators, in diesel locomotive engines, in boiler water, sea-water ship ballast, etc.

The term "dithiolium compounds" includes 1,2-dithiolium compounds and derivatives thereof such as salts, quaternaries, etc.

The amount of thiophosphate employed in treating the corrosive systems of this invention will vary with the particular compound employed, the particular system, the solids present in the system, the degree of corrosivity of the system, etc. A minor amount of the compound is generally employed sufficient to impart corrosion protection to the system. In general one employs concentration of trace amounts such as from about 1.0 p.p.m. to 10,000 p.p.m., for example from 5 to 5,000 p.p.m., such as from 100 to 2,500 p.p.m., but preferably from 500 to 2,000 p.p.m. In practice, concentrations of 1,000 ± 2000 p.p.m., are employed.

As is quite evident, new thiophosphates of this invention will be constantly developed which could be useful in this invention. It is, therefore, not only impossible to attempt a comprehensive catalogue of such compositions, but to attempt to describe the invention in its broader aspects in terms of specific chemical names used would be too voluminous and unnecessary since one skilled in the art could be following the description of the invention herein select a useful dithiolethione compound. This invention lies in the use of suitable thiophosphates as corrosion inhibitors in aqueous and-/or oxygenated and/or acid systems and their individual compositions are important only in the sense that their properties can affect this function. To precisely define each specific useful thiophosphate and aqueous system in light of the present disclosure would merely call for knowledge within the skill of the art in a manner analogous to a mechanical engineer who prescribes in the construction of a machine the proper materials and the proper dimensions thereof. From the description in this specification and with the knowledge of a chemist, one will know or deduce with confidence the applicability of specific thiophosphates suitable for this invention by applying them in the process set forth herein. In analogy to the case of a machine, wherein the use of certain materials of construction or dimensions of part would lead to no practical useful result, various materials will be rejected as inapplicable where others would be operative. I can obviously assume that no one will wish to use a useless thiophosphate nor will be misled because it is possible to misapply the teachings of the present disclosure to do so. Thus, any thiophosphate or mixtures containing them that can perform the function stated herein can be amployed.

Although the term monothiophosphate relates to the reaction product of phosphite esters, it is understood that the present invention also includes the use of thiophosphites as well as mixed oxygen-thiophosphites which react to yield polythiophosphates.

I claim:

1. The process of reverting thiophosphates of the formula

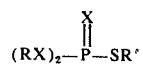

where X is O or S, R is a hydrocarbon radical from the group consisting of alkyl, aryl, cycloalkyl, aralkyl and alkaryl and R' is a 3-thione-propene-1 group of the formula

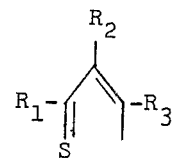

or

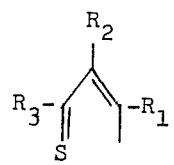

or where $R_1$, $R_2$ $R_3$ are hydrogen, alkyl, aryl, cycloalkyl, alkenyl, alkynyl, alkaryl, aralkyl or heterocyclic groups to the corresponding dithiolium compounds which comprises reacting said thiophosphates with an organic or inorganic acid.

2. The process of claim 1 where the thiophosphate is a monothiophosphate wherein R is an alkyl or aryl and the substituted 3-thionepentene-1 group is a 2-neopentyl-4,4-dimethyl-3-thione-pentene-1.

3. The process of claim 2 where the R substituent on the monothiophosphate is lower alkyl or phenyl.

4. The process of claim 1 where the acid used is an inorganic acid.

5. The process of claim 4 where the acid used is perchloric acid.

6. The process of claim 1 where the acid used is an organic acid.

7. A process which comprises dissolving O,O'-dimethyl-S-(2-neopentyl-4,4-dimethyl-3-thione-pentene-1) monothiophosphate in a solvent, adding to the solution perchloric acid and water, filtering off and drying the precipitate formed and recovering from said process the corresponding dithiolium compound.

* * * * *